United States Patent
Zhang et al.

(10) Patent No.: US 10,941,119 B2
(45) Date of Patent: Mar. 9, 2021

(54) METHOD FOR PREPARING IMIDAZOLIN-2 KETONE COMPOUND

(71) Applicant: SOOCHOW UNIVERSITY, Suzhou (CN)

(72) Inventors: Shilei Zhang, Suzhou (CN); Ye Liu, Suzhou (CN); Jing Jiang, Suzhou (CN); Yujian Mao, Suzhou (CN); Yanwei Hu, Suzhou (CN); Shaohua Chen, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 0 days.

(21) Appl. No.: 16/993,362

(22) Filed: Aug. 14, 2020

(65) Prior Publication Data
US 2020/0369622 A1  Nov. 26, 2020

Related U.S. Application Data

(63) Continuation of application No. PCT/CN2018/076907, filed on Feb. 14, 2018.

(51) Int. Cl.
*C07D 235/02* (2006.01)

(52) U.S. Cl.
CPC ................. *C07D 235/02* (2013.01)

(58) Field of Classification Search
None
See application file for complete search history.

(56) References Cited

U.S. PATENT DOCUMENTS 3,537,856 A  11/1970  Soma et al.

FOREIGN PATENT DOCUMENTS

CN  108358847 A  *  8/2018

OTHER PUBLICATIONS

Machine-generated English translation of Chinese patent No. CN108358847A, published on Aug. 3, 2018.*
Ito, Kazuaki et al. "Formations of azazulanones and dihydroazazulanones via reactions of troponimines with heterocumulenes." Heterocycles, vol. 41, No. 8, Dec. 31, 1995.
Yang, Kai, "Studies of the inverse electron demand Diels-Alder reactions of 1,3, 5-traizines with oximes, hydrazones or aldehydes/ketones as enamine (enol) dienophiles" Chinese Doctoral Dissertations Full-text Database, Engineering Science and Technology I, No. 8, Aug. 15, 2016.

* cited by examiner

*Primary Examiner* — Po-Chih Chen
(74) *Attorney, Agent, or Firm* — SZDC Law P.C.

(57) ABSTRACT

A method of preparing an imidazolin-2-tones compound includes: dissolving a cycloheptatrienone and an aromatic isocyanate in a solvent; and reacting the cycloheptatrienone and the aromatic isocyanate in the solvent without an oxidant and a catalyst to obtain the imidazolin-2-tone compound.

8 Claims, No Drawings

METHOD FOR PREPARING IMIDAZOLIN-2 KETONE COMPOUND

The present application is a Continuation Application PCT/CN2018/076907, filed on Feb. 14, 2018, which is incorporated by reference for all purposes as if fully set forth herein.

The application relates to the technical field of organic synthesis, and particularly, relates to a method of preparing imidazolin-2-tone compounds by reacting cycloheptatrienone with isocyanate.

BACKGROUND TECHNIQUE

Imidazolin-2-tone compounds are a very important part of o-diamine derivatives. Many bioactive molecules and synthetic intermediates contain imidazolin-2 ketone structures, such as dopamine D4 receptor antagonists, MurB inhibitors. Many of these CGRP receptor antagonists and antitumor drugs contain this structure. Conventionally, an imidazoline-2 ketone compound is usually cyclized by a compound such as an alpha-aminocarbonyl compound or a propargyl urea compound. Although there are many methods for synthesizing such compounds, there are still many problems. These methods generally require the participation of stoichiometric or catalytic amounts of expensive transition metal catalysts and oxidizing agents, which adds additional cost and environmental pollution. The source of nitrogen is also relatively limited.

SUMMARY OF INVENTION

Technical Problem

The technical problem of the invention is to provide a simple and economical method of preparing imidazolin-2-tones compounds that uses cycloheptatrieneono and isocyanate as raw materials. It has better atom economy and step economy. And it is an effective method to synthesize imidazoline-2-tones. In particular, the invention realizes the technical means of synthesizing imidazoline-2-tones compound, and the products are directly obtained in the solvent without adding oxidants or catalysts.

Technical Solution

In order to achieve the purpose of the invention, the technical scheme adopted in the invention is as follows, A method of preparing imidazolin-2-tone compounds includes the following steps: dissolving a cycloheptatrienone and an aromatic isocyanate in a solvent; and reacting the cycloheptatrienone and the aromatic isocyanate in the solvent without an oxidant or a catalyst to obtain the imidazolin-2-tone compound.

In the technical scheme above, the chemical formula of aromatic isocyanate was ArNCO, wherein the substituting group of Ar was aromatic group or substituted aryl.

In the technical scheme above, the solvent is an anhydrous solvent: triglyme, dimethyl sulfoxide, DMI, tetraglyme or bis(2-ethyl-hexyl)adipate and so on, preferably, triglyme.

Preferably, dissolving cycloheptatrienone and aromatic isocyanate into the anhydrous solvents, the temperature of reaction was 100° C. to 250° C. and the time of reaction was 0.5 to 5 hours, and obtaining the imidazolin-2-tone compound after extraction, evaporating to dryness, column chromatography to purify the compounds.

In the technical scheme above, the molar ratio of the cycloheptatrienone and isocyanate is 1:(2 to 6), preferably 1:(3-5), more preferably to 1:4.

In the technical scheme above, the temperature of reaction is 100° C. to 250° C. and the time of reaction is 0.5 to 5 hours. Preferably, the temperature of reaction is 120° C. to 200° C. and the time of reaction is 0.5 to 2 hours. More preferably, the temperature of reaction is 120° C. or 180° C. and the time of reaction is 1 hour.

Preferably, the substituting group of Ar is an aromatic group or a substituted aryl.

The invention also discloses the application of cycloheptatrienone and isocyanate were as raw materials in the preparation of compound.

Preferably, the application was underway in the reaction environment of oxidant-free, catalyst-free.

The chemical structure formula of imidazolin-2-tones compound was prepared by the invention is as follows:

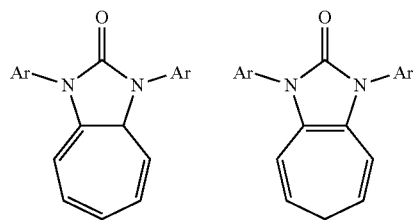

The technical scheme above can be expressed as follows:

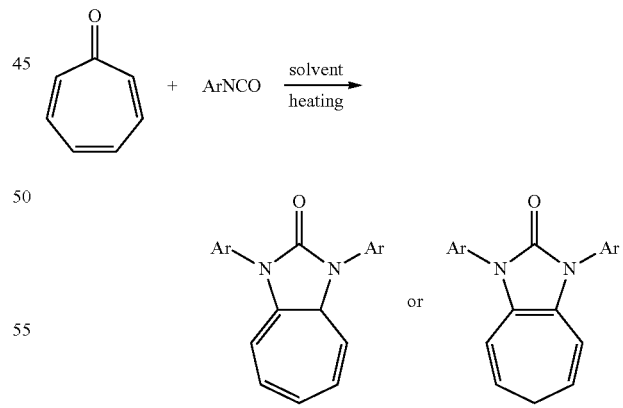

Advantageous Effects of the Invention

The invention disclosed a method of preparing imidazolin-2-tones compound for the first time. It is a simple method to prepare imidazolin-2-tones compound. The reaction condition is oxidant-free and catalyst-free.

INVENTION EMBODIMENT

Embodiments of the Invention

EXAMPLE 1

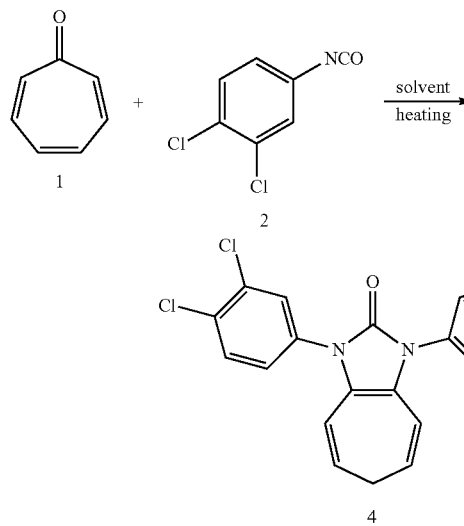

Dissolving compound 1 (53 mg, 0.5 mmol) and compound 2 (187 mg, 1 mmol, 2 equiv) into the tetraglyme, was heating at 250° C. for half an hour. When the solvent was cooled, added ethyl acetate, and then washed the organic layer by water for three times. After that merged the water layer, and washed the water layer by ethyl acetate layer once, and then merged the organic layer, washed the organic layer by saturated salt water, and dried it with anhydrous sodium sulfate. And after that spun steam to dry, column chromatography, to obtain product 4 with a yield of 20%. $^1$H NMR (400 MHz, CDCl$_3$): δ 7.65 (s, 2H), 7.56 (d, J=8.4 Hz, 2H), 7.38 (d, J=8.1 Hz, 2H), 6.23 (d, J=9.4 Hz, 2H), 5.34 (dd, J=14.9, 6.9 Hz, 2H), 2.58 (t, J=6.3 Hz, 2H). $^{13}$CNMR (151 MHz, CDCl$_3$): δ 150.38, 134.11, 133.36, 131.55, 131.02, 127.65, 125.09, 124.43, 116.78, 116.75, 28.22. LR-MS (ESI): m/z 436.9 [M+H]+.

Dissolving compound 1 (53 mg, 0.5 mmol) and compound 2 (280 mg, 1.5 mmol, 3 equiv.) into the bis(2-ethylhexyl)adipate, was heating at 230° C. for 2 hours. When the solvent was cooled, added ethyl acetate, and then washed the organic layer by water for three times. After that merged the water layer, and washed the water layer by ethyl acetate layer once, and then merged the organic layer, washed the organic layer by saturated salt water, and dried it with anhydrous sodium sulfate. Column chromatography, to obtain product 4 with a yield of 23%.

Dissolving compound 1 (53 mg, 0.5 mmol) and compound 2 (467 mg, 2.5 mmol, 5 equiv) into the DMI, was heating at 210° C. for 3 hours. When the solvent was cooled, added ethyl acetate, and then washed the organic layer by water for three times. After that merged the water layer, and washed the water layer by ethyl acetate layer once, and then merged the organic layer, washed the organic layer by saturated salt water, and dried it with anhydrous sodium sulfate. Column chromatography to obtain product 4 with a yield of 63%.

Dissolving compound 1 (53 mg, 0.5 mmol) and compound 2 (374 mg, 2 mmol, 4 equiv) into the triglyme, was heating at 180° C. for 1 hour. When the solvent was cooled, added ethyl acetate, and then washed the organic layer by water for three times. After that merged the water layer, and washed the water layer by ethyl acetate layer once, and then merged the organic layer, washed the organic layer by saturated salt water, and dried it with anhydrous sodium sulfate. Column chromatography to obtain product 4 with a yield of 95%.

Dissolving compound 1 (53 mg, 0.5 mmol) and compound 2 (561 mg, 3 mmol, 6 equiv) into the DMSO, was heating at 140° C. for 4 hours. When the solvent is cooled, added ethyl acetate, and then washed the organic layer by water for three times. After that merged the water layer, and washed the water layer by ethyl acetate layer once, and then merged the organic layer, washed the organic layer by saturated salt water, and dried it with anhydrous sodium sulfate. Column chromatography to obtain product 4 with a yield of 19%.

EXAMPLE 2

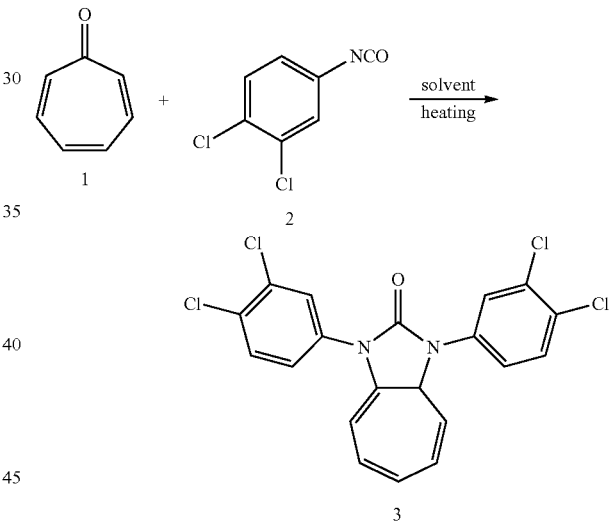

Dissolving compound 1 (53 mg, 0.5 mmol) and compound 2 (374 mg, 2 mmol, 4 equiv) into the DMI, was heating at 120° C. for 1.5 hours. When the solvent was cooled, added ethyl acetate, and then washed the organic layer by water for three times. After that merged the water layer, and washed the water layer by ethyl acetate layer once, and then merged the organic layer, washed the organic layer by saturated salt water, and dried it with anhydrous sodium sulfate. Column chromatography to obtain product 3 with a yield of 74%. $^1$H NMR (400 MHz, CDCl$_3$): δ 7.84 (s, 1H), 7.53-7.60 (m, 2H), 7.41-7.53 (m, 2H), 7.30 (s, 1H), 6.59 (dd, J=11.0, 6.8 Hz, 1H), 6.47 (dd, J=11.0, 5.8 Hz, 1H), 6.37-6.24 (m, 1H), 5.65 (d, J=6.2 Hz, 1H), 5.00 (dd, J=9.5, 2.8 Hz, 1H), 4.37 (s, 1H). $^{13}$C NMR (151 MHz, CDCl$_3$) δ 153.44, 137.02, 133.61, 133.55, 133.29, 132.41, 131.45, 131.28, 130.81, 129.31, 128.80, 127.37, 126.49, 126.19, 125.56, 120.43, 117.94, 116.06, 96.78, 56.96. LR-MS (ESI): m/z 436.9 [M+H]+.

EXAMPLE 3

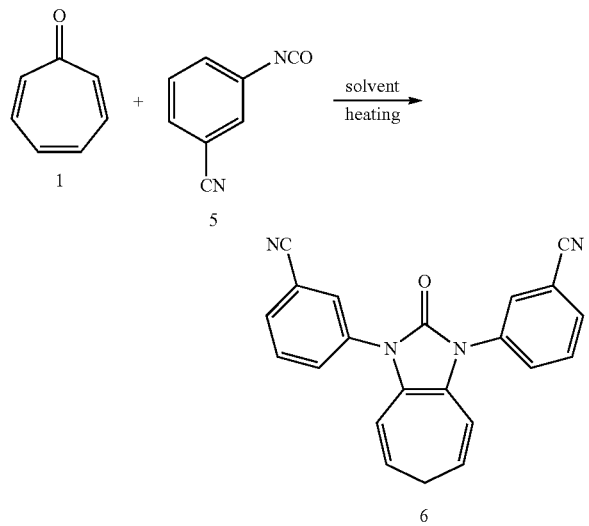

Dissolving compound 1 (53 mg, 0.5 mmol) and compound 2 (288 mg, 2 mmol, 4 equiv) into the anhydrous triglyme, was heating at 180° C. for 1 hour. When the solvent was cooled, added ethyl acetate, and then washed the organic layer by water for three times. After that merged the water layer, and washed the water layer by ethyl acetate layer once, and then merged the organic layer, washed the organic layer by saturated salt water, and dried it with anhydrous sodium sulfate. Column chromatography to obtain product 6 with a yield of 89%. $^1$H NMR (400 MHz, CDCl$_3$): δ 7.82 (d, J=9.3 Hz, 4H), 7.68-7.58 (m, 4H), 6.22 (d, J=9.4 Hz, 2H), 5.38 (dd, J=15.6, 7.2 Hz, 2H), 2.62 (t, J=6.7 Hz, 2H). $_{13}$C NMR (151 MHz, CDCl$_3$): δ 150.39, 135.64, 130.86, 130.42, 130.04, 128.89, 124.37, 117.98, 117.34, 116.63, 113.63, 28.20. LR-MS (ESI): m/z 351.1.

EXAMPLE 4

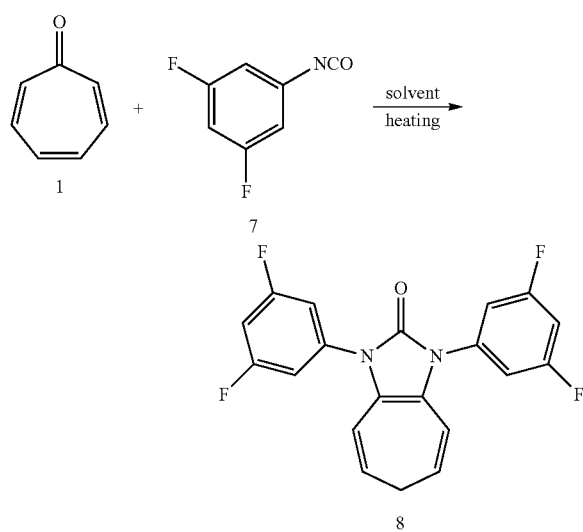

Dissolving compound 1 (53 mg, 0.5 mmol) and compound 7 (310 mg, 2 mmol, 4 equiv) into the anhydrous triglyme, was heating at 180° C. for 1 hour. When the solvent was cooled, added ethyl acetate, and then washed the organic layer by water for three times. After that merged the water layer, and washed the water layer by ethyl acetate layer once, and then merged the organic layer, washed the organic layer by saturated salt water, and dried it with anhydrous sodium sulfate. Column chromatography to obtain product 8 with a yield of 86%. $^1$H NMR (400 MHz, CDCl$_3$): δ 7.12 (d, J=6.1 Hz, 4H), 6.82 (t, J=8.7 Hz, 2H), 6.28 (d, J=9.5 Hz, 2H), 5.36 (dd, J=16.3, 7.1 Hz, 2H), 2.58 (t, J=6.9 Hz, 2H). $^{13}$C NMR (151 MHz, CDCl$_3$): δ 163.22 (dd, J=249.0, 14.2 Hz), 150.13 (s), 136.84 (t, J=12.8 Hz), 124.40 (s), 116.92 (s), 116.88 (s), 109.13 (dd, J=22.4, 6.4 Hz), 103.08 (t, J=25.3 Hz), 28.21 (s). LR-MS (ESI): m/z 373.0.

EXAMPLE 5

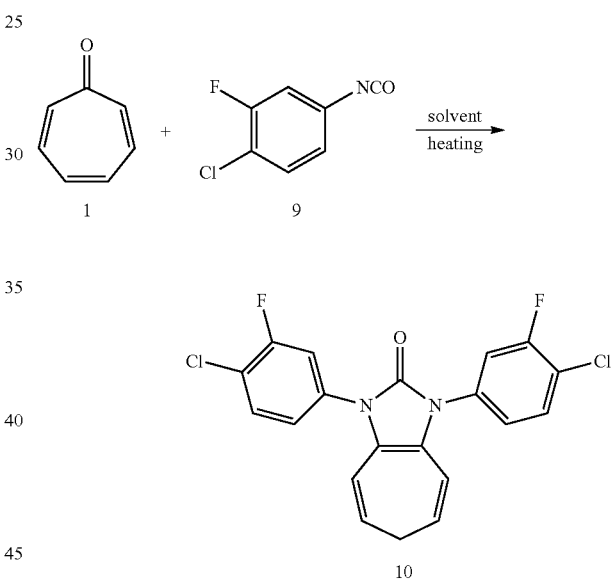

Dissolving compound 1 (53 mg, 0.5 mmol) and compound 9 (342 mg, 2 mmol, 4 equiv) into the anhydrous triglyme, was heating at 180° C. for 1 hour. When the solvent was cooled, added ethyl acetate, and then washed the organic layer by water for three times. After that merged the water layer, and washed the water layer by ethyl acetate layer once, and then merged the organic layer, washed the organic layer by saturated salt water, and dried it with anhydrous sodium sulfate. Column chromatography to obtain product 10 with a yield of 91%. $^1$H NMR (400 MHz, CDCl$_3$): δ 7.54-7.63 (m, 2H), 7.36-7.38 (m, 2H), 7.23 (d, J=8.8 Hz, 2H), 6.19 (d, J=9.5 Hz, 2H), 5.30 (dd, J=16.0, 7.0 Hz, 2H), 2.55 (t, J=6.8 Hz, 2H). $^{13}$C NMR (151 MHz, CDCl$_3$): δ 157.22 (d, J=250.3 Hz), 150.74 (s), 131.31 (d, J=3.5 Hz), 128.37 (s), 125.93 (d, J=7.4 Hz), 124.52 (s), 121.92 (d, J=18.9 Hz), 117.23 (d, J=22.4 Hz), 116.73 (s), 116.59 (s), 28.20 (s). LR-MS (ESI): m/z 405.1.

EXAMPLE 6

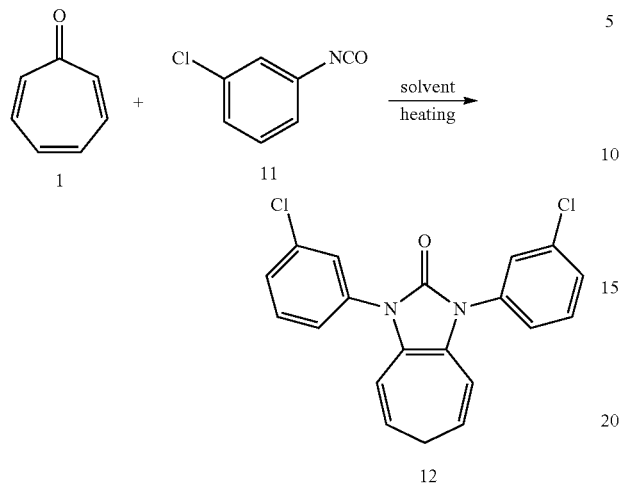

Dissolving compound 1 (53 mg, 0.5 mmol) and compound 11 (306 mg, 2 mmol, 4 equiv) into the anhydrous triglyme, was heating at 180° C. for 1 hour. When the solvent was cooled, added ethyl acetate, and then washed the organic layer by water for three times. After that merged the water layer, and washed the water layer by ethyl acetate layer once, and then merged the organic layer, washed the organic layer by saturated salt water, and dried it with anhydrous sodium sulfate. Column chromatography to obtain product 12 with a yield of 96%. $^1$H NMR (400 MHz, CDCl3): δ 7.54 (s, 2H), 7.42 (d, J=4.5 Hz, 4H), 7.34 (d, J=3.7 Hz, 2H), 6.24 (d, J=9.5 Hz, 2H), 5.31 (dd, J=16.1, 7.1 Hz, 2H), 2.57 (t, J=6.9 Hz, 2H). $^{13}$C NMR (151 MHz, CDCl$_3$): δ 150.63, 136.03, 134.96, 130.33, 127.67, 126.18, 124.59, 124.17, 117.08, 116.19, 28.22. LR-MS (ESI): m/z 369.1.

EXAMPLE 7

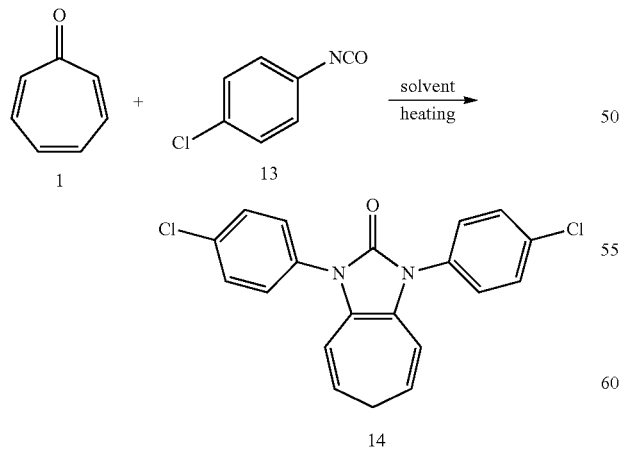

Dissolving compound 1 (53 mg, 0.5 mmol) and compound 13 (306 mg, 2 mmol, 4 equiv) into the anhydrous triglyme, was heating at 180° C. for 50 min. When the solvent was cooled, added ethyl acetate, and then washed the organic layer by water for three times. After that merged the water layer, and washed the water layer by ethyl acetate layer once, and then merged the organic layer, washed the organic layer by saturated salt water, and dried it with anhydrous sodium sulfate. Column chromatography, to obtain product 14 with a yield of 89%. $^1$H NMR (400 MHz, CDCl$_3$): δ 7.45 (s, 8H), 6.22 (s, 2H), 5.29 (s, 2H), 2.56 (s, 2H). $^{13}$C NMR (151 MHz, CDCl$_3$): δ 150.75, 133.44, 133.10, 129.56, 127.26, 124.59, 117.08, 115.96, 28.17. LR-MS (ESI): m/z 369.1.

EXAMPLE 8

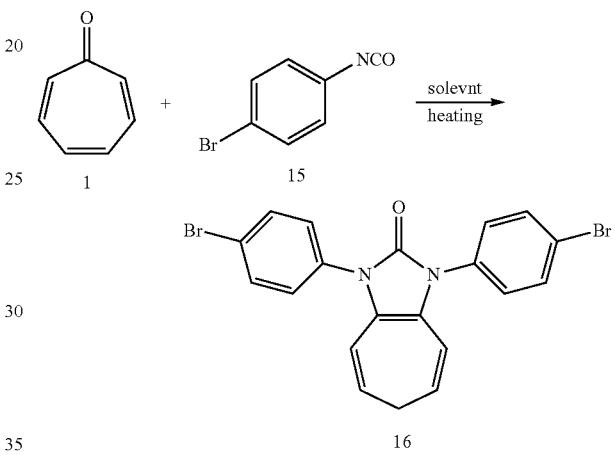

Dissolving compound 1 (53 mg, 0.5 mmol) and compound 15 (392 mg, 2 mmol, 4 equiv) into the anhydrous triglyme, was heating at 180° C. for 1H. When the solvent was cooled, added ethyl acetate, and then washed the organic layer by water for three times. After that merged the water layer, and washed the water layer by ethyl acetate layer once, and then merged the organic layer, washed the organic layer by saturated salt water, and dried it with anhydrous sodium sulfate. Column chromatography to obtain product 16 with a yield of 87%. $^1$H NMR (400 MHz, CDCl$_3$): δ 7.60 (d, J=8.2 Hz, 4H), 7.40 (d, J=8.3 Hz, 4H), 6.22 (d, J=9.5 Hz, 2H), 5.29 (dd, J=14.5, 8.3 Hz, 2H), 2.56 (t, J=6.7 Hz, 2H). $^{13}$C NMR (151 MHz, CDCl$_3$): δ 150.60, 133.93, 132.53, 127.53, 124.55, 121.02, 117.07, 116.01, 28.17. LR-MS (ESI): m/z 458.9.

EXAMPLE 9

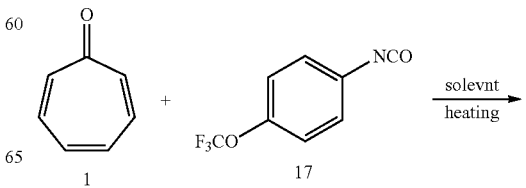

-continued

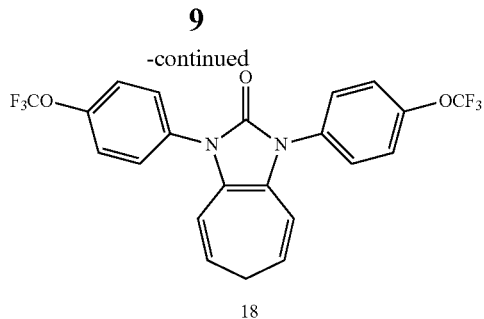

18

Dissolving compound 1 (53 mg, 0.5 mmol) and compound 17 (406 mg, 2 mmol, 4 equiv) into the anhydrous triglyme, was heating at 180° C. for 1H. When the solvent was cooled, added ethyl acetate, and then washed the organic layer by water for three times. After that merged the water layer, and washed the water layer by ethyl acetate layer once, and then merged the organic layer, washed the organic layer by saturated salt water, and dried it with anhydrous sodium sulfate. Column chromatography to obtain product 18 with a yield of 98%. $^1$H NMR (400 MHz, CDCl$_3$): δ 7.56 (d, J=8.7 Hz, 4H), 7.34 (d, J=8.4 Hz, 4H), 6.25 (d, J=9.5 Hz, 2H), 5.31 (dd, J=16.1, 7.0 Hz, 2H), 2.58 (t, J=6.8 Hz, 2H). $^{13}$C NMR (101 MHz, CDCl$_3$): δ 150.87 (s), 148.01 (s), 133.40 (s), 127.39 (s), 124.62 (s), 121.95 (s), 120.57 (q, J=257.7 Hz), 117.04 (s), 116.20 (s), 28.17 (s). LR-MS (ESI): m/z 469.1.

EXAMPLE 10

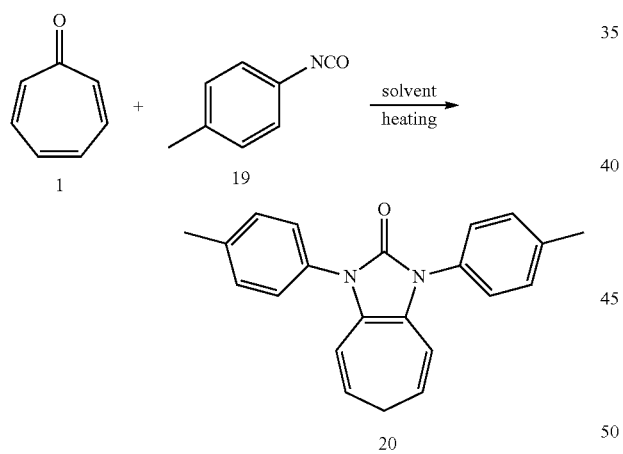

Dissolving compound 1 (53 mg, 0.5 mmol) and compound 19 (266 mg, 2 mmol, 4 equiv) into the anhydrous triglyme, was heating at 180° C. for 2H. When the solvent was cooled, added ethyl acetate, and then washed the organic layer by water for three times. After that merged the water layer, and washed the water layer by ethyl acetate layer once, and then merged the organic layer, washed the organic layer by saturated salt water, and dried it with anhydrous sodium sulfate. Column chromatography, to obtain product 20 with a yield of 89%. $^1$H NMR (400 MHz, CDCl$_3$): δ 7.39 (d, J=8.0 Hz, 4H), 7.28 (d, J=8.2 Hz, 4H), 6.24 (d, J=9.5 Hz, 2H), 5.24 (dd, J=16.1, 7.0 Hz, 2H), 2.55 (t, J=6.8 Hz, 2H), 2.40 (s, 6H). $^{13}$C NMR (101 MHz, CDCl$_3$): δ 151.23, 137.31, 132.44, 129.93, 126.15, 124.79, 117.39, 114.93, 28.13, 21.28. LR-MS (ESI): m/z 329.0.

EXAMPLE 11

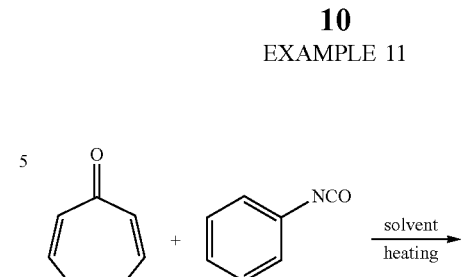

22

Dissolving compound 1 (53 mg, 0.5 mmol) and compound 21 (274 mg, 2 mmol, 4 equiv) into the anhydrous triglyme, was heating at 180° C. for 50 min. When the solvent was cooled, added ethyl acetate, and then washed the organic layer by water for three times. After that merged the water layer, and washed the water layer by ethyl acetate layer once, and then merged the organic layer, washed the organic layer by saturated salt water, and dried it with anhydrous sodium sulfate. Column chromatography, to obtain product 22 with a yield of 93%. $^1$H NMR (400 MHz, CDCl$_3$): δ 7.45 (dd, J=14.5, 7.3 Hz, 2H), 7.36-7.27 (m, 4H), 7.07 (t, J=7.8 Hz, 2H), 6.27 (d, J=9.4 Hz, 2H), 5.31 (dd, J=15.6, 7.2 Hz, 2H), 2.58 (t, J=6.6 Hz, 2H). $^{13}$C NMR (151 MHz, CDCl$_3$): δ 162.98 (d, J=247.1 Hz), 150.60 (s), 136.30 (d, J=10.2 Hz), 130.47 (d, J=9.1 Hz), 124.58 (s), 121.55 (d, J=3.0 Hz), 117.14 (s), 116.05 (s), 114.44 (d, J=21.0 Hz), 113.46 (d, J=24.3 Hz), 28.16 (s). LR-MS (ESI): m/z 337.0.

EXAMPLE 12

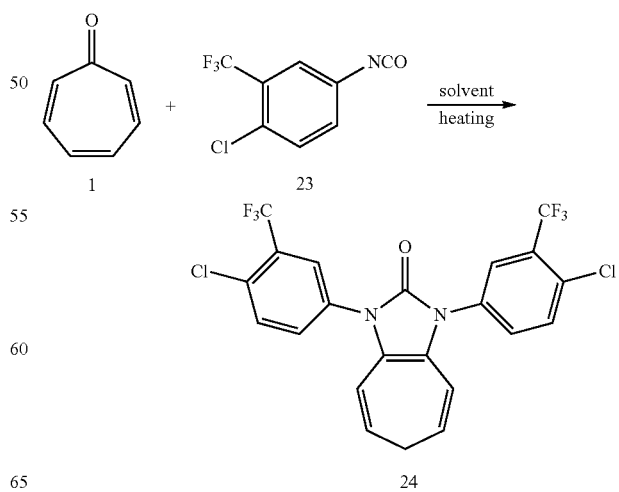

24

Dissolving compound 1 (53 mg, 0.5 mmol) and compound 23 (442 mg, 2 mmol, 4 equiv) into the anhydrous triglyme, was heating at 180° C. for 1H. When the solvent was cooled, added ethyl acetate, and then washed the organic layer by water for three times. After that merged the water layer, and washed the water layer by ethyl acetate layer once, and then merged the organic layer, washed the organic layer by saturated salt water, and dried it with anhydrous sodium sulfate. Column chromatography, to obtain product 24 with a yield of 96%. $^1$H NMR (400 MHz, CDCl$_3$): δ 7.87 (s, 2H), 7.60-7.72 (m, 4H), 6.22 (d, J=9.5 Hz, 2H), 5.38 (dd, J=16.0, 7.1 Hz, 2H), 2.62 (t, J=6.8 Hz, 2H). $^{13}$C NMR (101 MHz, CDCl$_3$): δ 150.44 (s), 133.55 (s), 132.59 (s), 131.10 (s), 129.94 (s), 129.61 (q, J=32.0 Hz), 124.90 (q, J=5.2 Hz), 124.43 (s), 122.46 (q, J=273.6 Hz), 117.29 (s), 116.54 (s), 28.27 (s). LR-MS (ESI): m/z 505.1.

EXAMPLE 13

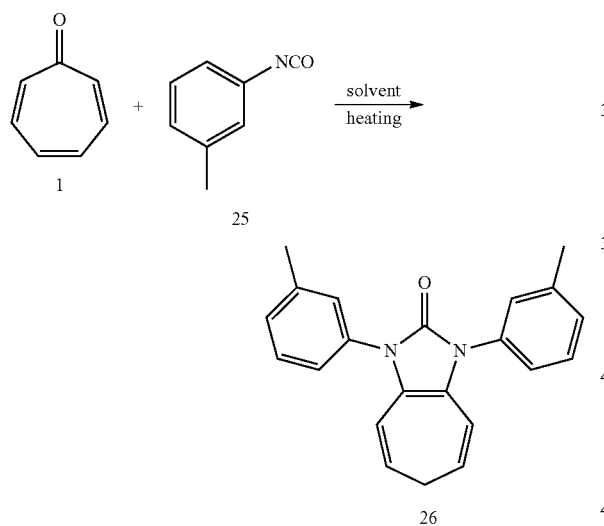

Dissolving compound 1 (53 mg, 0.5 mmol) and compound 25 (266 mg, 2 mmol, 4 equiv) into the anhydrous triglyme, was heating at 180° C. for 2H. When the solvent was cooled, added ethyl acetate, and then washed the organic layer by water for three times. After that merged the water layer, and washed the water layer by ethyl acetate layer once, and then merged the organic layer, washed the organic layer by saturated salt water, and dried it with anhydrous sodium sulfate. Column chromatography, to obtain product 26 with a yield of 97%. $^1$H NMR (400 MHz, CDCl$_3$): δ 7.33-7.40 (m, 4H), 7.28 (d, J=9.1 Hz, 2H), 7.17 (d, J=7.4 Hz, 2H), 6.25 (d, J=9.5 Hz, 2H), 5.25 (dd, J=16.0, 7.1 Hz, 2H), 2.57 (t, J=6.8 Hz, 2H), 2.42 (s, 6H). $^{13}$C NMR (151 MHz, CDCl$_3$): δ 151.13, 139.32, 134.93, 129.05, 128.25, 126.95, 124.80, 123.29, 117.45, 114.98, 28.15, 21.52. LR-MS (ESI): m/z 329.0.

EXAMPLE 14

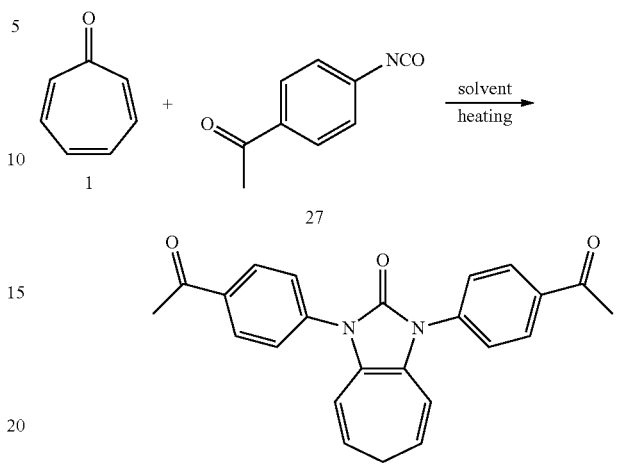

Dissolving compound 1 (53 mg, 0.5 mmol) and compound 27 (322 mg, 2 mmol, 4 equiv) into the anhydrous triglyme, was heating at 180° C. for 70 min. When the solvent was cooled, added ethyl acetate, and then washed the organic layer by water for three times. After that merged the water layer, and washed the water layer by ethyl acetate layer once, and then merged the organic layer, washed the organic layer by saturated salt water, and dried it with anhydrous sodium sulfate. Column chromatography, to obtain product 28 with a yield of 95%. $^1$H NMR (400 MHz, CDCl$_3$) δ 8.08 (d, J=8.1 Hz, 4H), 7.66 (d, J=8.1 Hz, 4H), 6.27 (d, J=9.4 Hz, 2H), 5.34 (dd, J=15.6, 7.1 Hz, 2H), 2.63 (s, 8H). $^{13}$C NMR (101 MHz, CDCl$_3$): δ 197.14, 150.43, 138.97, 135.59, 129.55, 125.38, 124.63, 117.23, 116.45, 28.20, 26.79. LR-MS (ESI): m/z 385.1.

EXAMPLE 15

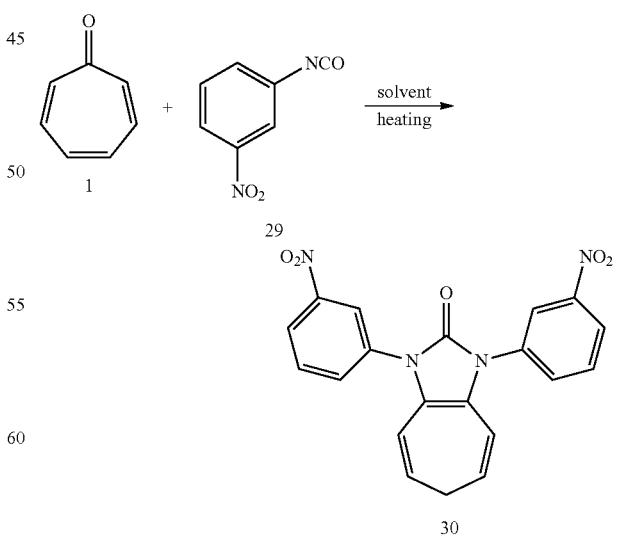

Dissolving compound 1 (53 mg, 0.5 mmol) and compound 29 (328 mg, 2 mmol, 4 equiv) into the anhydrous triglyme, was heating at 180° C. for 60 min. When the solvent was cooled, added ethyl acetate, and then washed the organic layer by water for three times. After that merged the water layer, and washed the water layer by ethyl acetate layer once, and then merged the organic layer, washed the organic layer by saturated salt water, and dried it with anhydrous sodium sulfate. Column chromatography, to obtain product 30 with a yield of 99%. $^1$H NMR (400 MHz, CDCl$_3$): δ 8.42 (s, 2H), 8.23 (d, J=8.1 Hz, 2H), 7.95 (d, J=7.9 Hz, 2H), 7.70 (t, J=8.1 Hz, 2H), 6.27 (d, J=9.5 Hz, 2H), 5.41 (dd, J=16.1, 7.1 Hz, 2H), 2.66 (t, J=6.9 Hz, 2H). $^{13}$C NMR (151 MHz, CDCl$_3$): δ 150.47, 148.88, 135.89, 131.57, 130.34, 124.46, 122.17, 120.64, 117.57, 116.55, 28.31. LR-MS (ESI): m/z 391.0.

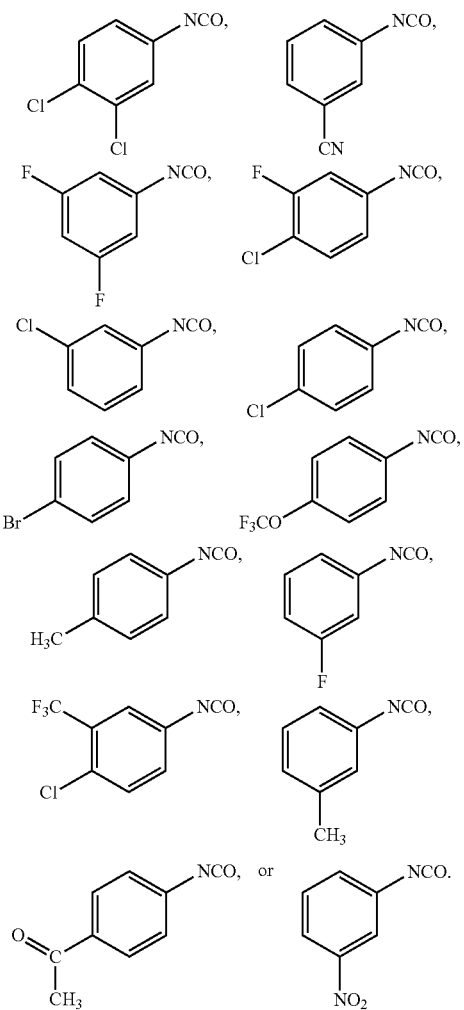

The invention claimed is:

1. A method of preparing an imidazolin-2-tone compound, comprising the following steps:
   dissolving a cycloheptatrienone and an aromatic isocyanate in a solvent; and
   reacting the cycloheptatrienone and the aromatic isocyanate in the solvent without an oxidant or a catalyst to obtain the imidazolin-2-tone compound.

2. The method of according to claim 1, wherein the chemical formula of the aromatic isocyanate is ArNCO, and Ar is an aryl group or a substituted aryl group.

3. The method according to claim 1, wherein the solvent is triglyme, dimethyl sulfoxide, DMI (1,3-dimethyl-2-imidazolidinone), tetraglyme or bis(2-ethyl-hexyl)adipate.

4. The method of according to claim 1, wherein a molar ratio of the cycloheptatrienone and the aromatic isocyanate is from 1:2 to 1:6.

5. The method according to claim 4, wherein the molar ratio of the cycloheptatrienone and the aromatic isocyanate is from 1:3 to 1:5.

6. The method according to claim 1, wherein a reaction temperature is 100° C. to 250° C. and a reaction time is 0.5 to 5 hours.

7. The method according to claim 6, wherein the reaction temperature is 120° C. to 200° C. and the reaction time is 0.5 to 2 hours.

8. The method according to claim 2, wherein the aromatic isocyanate is